United States Patent [19]
James et al.

[11] Patent Number: 6,130,252
[45] Date of Patent: Oct. 10, 2000

[54] INSECTICIDE AND INSECT REPELLANT COMPOSITIONS

[76] Inventors: Lynn Sue James, 33 Main St., Newtown, Conn. 06470; Michael A. Siedman, Laurel Trail, Sandy Hook, Conn. 06482

[21] Appl. No.: 08/949,879

[22] Filed: Oct. 14, 1997

Related U.S. Application Data

[62] Division of application No. 08/523,821, Sep. 6, 1995, Pat. No. 5,681,859, which is a division of application No. 08/130,664, Oct. 1, 1993, abandoned.

[51] Int. Cl.[7] .......................... A01N 37/18; A01N 37/20; A61K 31/16; A61K 31/164
[52] U.S. Cl. .......................... 514/625; 514/616; 514/627; 514/629; 514/667; 514/669; 514/919; 424/78.02; 424/78.08; 424/78.37; 424/DIG. 10
[58] Field of Search ...................................... 514/574, 553, 514/557, 558, 560, 561, 563, 564, 625, 627, 629, 646, 663, 665, 667, 669, 616, 919; 424/195.1, 78.02, 78.08, 78.37, DIG. 10

[56] References Cited

U.S. PATENT DOCUMENTS

| | | |
|---|---|---|
| 4,323,582 | 4/1982 | Siegel et al. ..................... 424/DIG. 10 |
| 5,015,665 | 5/1991 | Steltenkamp ............................. 514/625 |
| 5,594,029 | 1/1997 | Bencsits .................................. 514/552 |

OTHER PUBLICATIONS

Promt Abstract 94: 533461, 1994.

*Primary Examiner*—John Pak
*Attorney, Agent, or Firm*—Melvin I. Stoltz

[57] ABSTRACT

A non-toxic, environmentally safe and easily employable insecticide and insect repellant is achieved by providing an aqueous composition incorporating ethanolamine based compounds, either independently or in combination with the ethanolamine based compounds being selected from both simple compounds and conjugated compounds. In one preferred embodiment, a highly effective composition is attained for safe, effective, direct topical application to humans and animals by employing between about 10% and 70% by volume of the entire composition of the ethanolamine-based compound. In alternate preferred embodiments, the insecticide is formulated for application to plants, trees, crops, and other vegetation to provide a composition which effectively controls bothersome insects, while being completely safe and non-injurious to the plant, tree, or crop, as well as to the flowers or fruit thereof. In addition, the compositions of this invention are completely biodegradable, and are safe to the environment and water supplies.

5 Claims, No Drawings

INSECTICIDE AND INSECT REPELLANT COMPOSITIONS

This application is a division of application Ser. No. 08/523,821 filed Sep. 6, 1995, which application is now U.S. Pat. No. 5,681,859, which is a division of U.S. Ser. No. 08/130,664, filed Oct. 1, 1993, now abandoned.

TECHNICAL FIELD

This invention relates to pesticides, insecticides and insect repellant compositions and, more particularly, to such compositions which are highly effective in killing a wide range of insects while also being non-toxic to humans, animals, and the environment.

BACKGROUND ART

Substantial effort has been expended by a wide variety of entities in attempting to develop highly effective pesticides, particularly insecticide and/or insect repellents, which are capable of eradicating or controlling insects which destroy ornamental and agricultural plants, crops, trees, etc. or which attack, harm, or annoy humans and animals. Particularly bothersome for humans and animals are blood-sucking insects, such as mosquitos, ticks, fleas, lice, etc. These insects are annoying as well as possibly harmful due to the potential transmission of diseases. Although substantial need has existed in the industry for products which control or eradicate these insects, prior art attempts have failed to provide effective formulations which are capable of fully eradicating or controlling insects, while also being non-toxic to humans and animals.

In an attempt to meet the consumer demand for products of this nature, various pesticides, insecticides and insect repellant formulations have been developed. However, these prior art formulations typically incorporate active ingredients which are highly toxic to humans and to many animals. Consequently, the usable concentration of these toxic chemicals must be reduced, typically to the point of rendering the resulting formulation ineffective in providing the desired killing effect.

Another problem that exists with prior art pesticides is the ability of the insects to become resistant or immune to the pesticide. Due to the highly adaptive nature of most insects and the manner in which pesticides typically function, many prior art insecticides are effective initially, but lose their effectiveness over time due to insect developed immunity or resistance.

Insects which cause injury to plants, crops, trees, food supplies, humans and animals have existed for centuries and have always been considered as pests. Virtually all of these pests are members of the *phylum Arthropoda*, which comprises about 75% of known animal species. More than 930,000 arthropod species have been described and over 6,000,000 species are estimated to exist.

Of particular importance to the present invention are the species of arthropods found in the classes Insecta, Arachnida, Anoplura, and Siphonaptera. The need for pest control by developing pesticides dates back to ancient times, where fumigation was employed in an attempt to control pests on plant growth. In this century, numerous chemical formulations have been developed. Initially, inorganic metallic compounds were used as the principal active ingredients. More recently, purely organic pesticides have been employed.

One most well-known organic pesticide which has been developed and which had been particularly effective is dichlorodiphenyltrichloroethane (DDT). Although this compound was found to have extraordinary insecticidal properties and had been widely used as one of the most effective pesticides, its use has now been banned in the United States and in other countries due to its more recently discovered toxicity to humans and animals.

Following the discovery of the efficacy of DDT, numerous other organochlorides, such as cyclodienes were developed as practical pesticides, with further discoveries revealing organophosphate compounds as highly effective pesticides. However, as use of these chemical compounds grew, the deleterious effects of these compounds were also discovered and their use was restricted.

Another group of pesticides that have been employed in the prior art comprise pyrethroids or pyrethrins. Compounds, coming within this classification, have been widely used in a wide variety of insecticides and insect repellant products. However, although originally effective, the pyrethroids are examples of pesticides which are now increasingly ineffective, due to acquired resistance by the insects. Presently, many insects have developed resistance or immunity to the insecticidal effect of the pyrethroids and, as a result, these compounds are increasingly unusable for effectively controlling undesirable insects and pests.

While other attempts have been made to eliminate the toxicity of pesticides or develop non-toxic pesticides, these attempts have failed to provide a completely effective, non-toxic pesticide. In particular, most of these prior art pesticides are non-biodegradable, causing the pesticide to continuously build up in the soil and, subsequently, in the food chain. This long-term build up has been found to be particularly hazardous to the long-term health of the population. As a result, use of many such pesticides has been either banned or severely restricted by recent legislation.

Although the need for an effective, non-toxic, biodegradable pesticide has existed for decades, an effective pesticide has not been realized. As an alternative, non-chemical methods have been used. However, little success has been attained with non-chemical methods. As a result, in addition to these non-chemical methods, pesticides continue to be used in limited concentrations with reduced efficacy.

Therefore, it is a principal object of the present invention to provide an effective pesticide which is capable of providing long-term control and eradication of a wide range of insects which attack or feed on plants, crops, trees, animals, and humans without harming the plants, crops, trees, animals, or humans coming in contact with the pesticide.

Another object of the present invention is to provide a pesticide having the characteristic features described above which is completely non-toxic to humans, animals, and the environment.

Another object of the present invention is to provide a pesticide which effectively functions as an insecticide for killing a wide range of insects as well as an acaricide for controlling lice, mites and ticks.

Another object of the present invention is to provide an insecticide having the characteristic features described above which is completely biodegradable and completely safe for application directly to desired plants, humans and animals.

A further object of the present invention is to provide an insecticide having the characteristic features described above which is not harsh or irritating to the skin of humans and animals and can be safely applied, without harm, to skin, scalp, or hair.

Another object of the present invention is to provide an insecticide having the characteristic features described above which kills insects in a manner that prevents the insects from developing a resistance or immunity thereto.

Another object of the present invention is to provide an insecticide having the characteristic features described above which can be employed as an insect repellant without harmful side effects to the user.

Another object of the present invention is to provide an insecticide having the characteristic features described above which has no adverse effects on the food products produced by treated plants, crops, and trees, as well as no adverse effect on the soil or water.

Other and more specific objects will in part be obvious and will in part appear hereinafter.

DETAILED DESCRIPTION

By employing the present invention, all of the prior art difficulties and drawbacks are completely eliminated and a safe, effective pesticide is attained. As detailed herein, the compositions of the present invention are particularly constructed for controlling insects and other members of the phylum arthropoda. In this regard, in addition to effectively controlling all conventional, harmful, and annoying insects, the compositions of the present invention also effectively control insects such as mites, ticks and lice. As a result, these compositions also function as acaracides, in addition to being insecticides. Consequently, it is to be understood that the use of the terms pesticides, insecticides and insect repellents are used interchangeably herein to broadly define the wide range of "pests" for which the present invention is effective.

In addition to its broad applicability, the compositions of the present invention provides safe and highly effective insecticides, while also providing compositions which are non-toxic to humans, animals, and the environment. The compositions of this invention are non-toxic and fully biodegradable, causing no harm or injury to humans, animals, or water systems.

The chemical formulations of the present invention comprise organic compounds which have been uniquely combined to attain highly effective insecticide compositions previously unattainable by this industry. Although the individual organic compounds employed in the compositions of the present invention are generally well-known and have been widely used, the unique, novel and unobvious combination of these organic compounds achieves novel and unobvious compositions which provide a synergistic result and attain insecticide formulations which overcome all of the prior art difficulties and objections that have plagued the pesticide industry for decades.

By employing the unique chemical compositions of the present invention, insecticides and insect repellents are attained which are highly effective in controlling a wide range of insects that have previously wrecked havoc with plants, trees, crops, humans, and animals. In particular, the chemical formulations of the present invention function as contact sprays capable of killing insects virtually on contact, as well as lotions and shampoos for direct application to skin or hair.

In the composition of the present invention, avoidance of insect resistance or immunity is achieved by establishing insecticide compositions which are incapable of being rendered ineffective by subsequently developed resistance or immunity. In the present invention, the compositions of the present invention kill the undesirable insects by creating a barrier, such as a film, or creating a reaction which inhibits and/or blocks the transfer of gases in the sensitive trachea of the insects. In this way, the compositions of the present invention kill the insects by interfering with the respiratory system of the insects. As a result, insects are incapable of developing an immunity or resistance to the compositions of this invention and long-term, effective use is assured.

Regardless of the method of application, the compositions of this invention have been found to be highly effective in killing stink bugs, caterpillars, a wide variety of ants, most flies, including fruit flies and white flies in particular, aphids, mealy bugs, mosquitoes, lice, mites, ticks, and the like. All of these insects are classified in the *phylum Arthropoda*, with most being in the class Insecta, Arachnida, Anoplura and Siphonaptera. The Insecta class is the largest and most diverse class in the animal kingdom, with over 750,000 different described species and an actual number of living species estimated to be three million. Although the insects identified above are not all inclusive, they represent the various principal classes, orders and families of arthropods against which the chemical compositions of the present invention have proven to be highly effective.

The insecticide compositions of the present invention are safely employed on humans, animals, plants, trees, crops, fruit trees and the like, as well as functioning as an effective general household product. One of the particular unique aspects of the compositions of the present invention is the ability of these compositions to function as highly effective insecticides, killing the wide variety of insects sought to be eradicated or controlled, while also being completely biodegradable and non-toxic to humans, animals and the environment, particularly the water systems. In addition, as detailed below, virtually every plant, tree, and crop upon which the chemical compositions of the present invention have been employed experienced virtually no adverse effects, while having the undesirable insects successfully eliminated.

Another unique aspect of the pesticide compositions of the present invention is the attainment of a highly effective and efficient pesticide which employs organic chemical compounds commonly employed in cosmetic products. As a result, the chemical compounds incorporated into the pesticide compositions of the present invention have all been used in cosmetic compositions approved by the FDA for safe use by humans. By employing this class of ingredients, the non-toxic safety of the resulting compositions is apparent and the ability to employ these compositions without in any way harming humans, animals, or the environment is readily apparent.

In view of the unique use of chemical compounds which have been commonly employed in the cosmetic field, the following detailed disclosure provides both the accepted chemical names of the ingredients, as well as the name employed for each compound or ingredient by the Cosmetic, Toiletry, and Fragrance Association (CTFA), as found in the *CTFA International Cosmetic Ingredient Dictionary, Fourth Edition*. In this way, a full and complete disclosure of each and every chemical compound is provided.

Although the chemical compounds in the pesticide compositions of the present invention are individually commonly employed in cosmetic compositions, the use of these compounds as a pesticide represents a unique and unobvious departure from prior art teachings. Although these compounds have been commonly employed in products, there is no teaching or suggestion in the prior art that these products can be employed or combined in the manner detailed herein to attain the highly effective pesticide compositions achieved by the present invention.

In the present invention, it has been found that by employing one or more ethanolamine based compounds, in the manner detailed herein, all of the prior art difficulties and drawbacks are eliminated. In accordance with the teaching of the present invention, it has been found that the ethanolamine based compounds capable of attaining the results detailed herein are defined by Formula I, detailed below:

FORMULA I

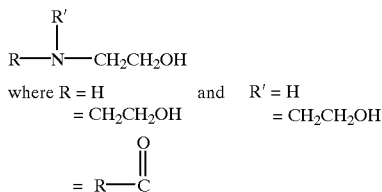

In addition to employing one or more ethanolamine formatives as defined by Formula I, effective compositions can also be attained by employing one of the ethanolamine formatives defined by Formula I in a conjugated form. Preferably, the conjugated compound is selected from the group consisting of lauryl sulfuric acid and substituted aromatic compounds. In this regard, the preferred compounds employed for conjugation comprise one selected from the group consisting of compounds having the following formula:

$$CH_3(CH2_{10}CH_2R''SO_3H$$

where R" is an oxygen molecule or a benzene ring.

One of the principal formatives of Formula I employed as an ingredient of the pesticides of the present invention is mono-ethanolamine. Mono-ethanolamine has the CTFA designation ethanolamine and is the monoamine that conforms to the formula:

$$NH_2CH_2CH_2OH$$

Mono-ethanolamine is also known as 2-aminoethanol.

Other formatives of Formula I which have been found to be most effective in forming the compositions of the present invention include diethanolamine and triethanolamine. Diethanolamine is the aliphatic amine that conforms to the following formula:

$$HN(CH_2CH_2OH)_2$$

Triethanolamine, also designated as TEA, is an alkanolamine that conforms to the following formula:

$$N(CH_2CH_2OH)_3$$

Several other formatives of Formula I have been found to be particularly effective in providing pesticide compositions in accordance with the present invention. These additional formatives are Coconut Polydiethanolamide, Coconut Diethanolamide (Cocamide DEA), Triethanolamine Lauryl Sulfate (TEA Lauryl Sulfate) and Triethanolamine Dodecylbenzenesulfonate (TEA Dodecylbenzenesulfonate).

Coconut Diethanolamide is a mixture of ethanolamides of coconut acid and has the following general formula:

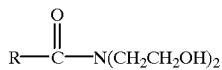

where RCO represents the fatty acids derived from coconut oil.

The chemical formula for coconut polydiethanolamide is presently unknown. However, it is believed that this composition is structurally similar to Coconut Diethanolamide and incorporates fatty acid radicals derived from coconut oil. However, coconut polydiethanolamide comprises a free amine radical that ranges between about 20% to 25% of the total composition. This compound is available under the trade name Compelan PD and is sold by Henkel Corporation of Hoboken, N.J.

Triethanolamine Lauryl Sulfate is the triethanolamine salt of lauryl sulfuric acid. This compound has the following general formula:

$$CH_3(CH_2)_{10}CH_2OSO_3H.N(CH_2CH_2OH)_3$$

Triethanolamine Dodecylbenzenesulfonate is the substituted aromatic compound and has the following general formula:

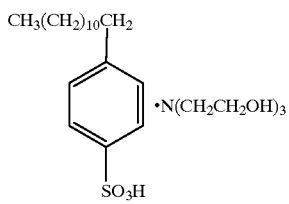

These latter two compounds represent the preferred formatives of Formula I which are employed as conjugated compounds.

As fully detailed herein, by employing aqueous solutions of one or more ethanolamine formatives defined by Formula I, either independently or in combination, highly effective pesticides are attained which completely eliminate all of the prior art drawbacks and difficulties that have been incapable of being effectively satisfied. In addition, all of the insecticide compositions of the present invention are non-toxic to humans, animals, and the environment, enabling the insecticides to be freely used, in accordance with application instructions, without any adverse reactions occurring.

As detailed herein, the non-toxic, safe insecticides of the present invention have been proven to be highly effective in eliminating virtually all type of insects in the phylum Arthropod, particularly, those insects which have plagued humans, animals, plants, crops, trees, and the like. In addition, the compositions of the present invention operate in a manner which prevents the insects from developing an immunity or resistance thereto. Consequently, a safe, effective pesticide is achieved which can be used repeatedly without fear of the composition becoming ineffective.

In Table I, an overall formulation for an insecticide composition is provided which has been found to be effective for use on humans and animals. Due to the gentle, non-toxic nature of the compositions detailed in Table I, application directly to the skin or hair of humans or animals is easily attained without any adverse reactions. Furthermore, since these insecticide compositions can be employed directly on the skin surface, this composition can be used as an insect repellant as well as an insecticide.

TABLE I

Insecticide Composition for Use on Humans and Animals

| Ingredients | % by Volume |
|---|---|
| Compound of Formula I | 10–70 |
| Water | 30–90 |

In achieving a highly effective insecticide or insect repellent for use on humans, it has been found that the Compound of Formula I employed in this composition preferably comprises one or more selected from the group consisting of Mono-ethanolamine, Diethanolamine, Triethanolamine, Coconut Diethanolamide, and Coconut Polydiethanolamide. Generally, the mono-ethanolamine, diethanolamine, triethanolamine, coconut diethanolamide or coconut polydiethanolamide can be employed virtually interchangeably, either individually or in combination, within the percent ranges detailed in Table I.

Although the use of any of these compounds, either independently or in combination achieves a highly effective insecticide, it has been found that mono-ethanolamine can be irritating to the eyes and mucus membranes, when used in higher concentrations. However, this compound has been found to provide a beneficial healing effect when applied to skin surfaces. Consequently, any formulation created for use on humans preferably does not include mono-ethanolamine, or does not include mono-ethanolamine in any quantity which would cause adverse reactions. In addition, mono-ethanolamine bearing compositions are employed on skin surfaces only, with care being exercised to prevent any contact with eyes, noses, or other mucus membranes.

It has also been found that although each of the preferred compounds detailed above can be used virtually interchangeably in order to attain any effective insecticide composition, coconut diethanolamine is preferred. In test results which are detailed below, coconut ethanolamide has been most effectively employed in the composition in the lowest concentration while still providing a highly effective insecticide composition. Consequently, although the other compounds detailed above can be employed with equal efficacy, a greater quantity of the other compounds may be required to attain an insecticide composition having equal capabilities.

In order to effectively apply the insecticide compositions defined in Table I, the compositions can be formed as a lotion, spray, or shampoo. As detailed below, experiments have proven that these compositions are completely effective in eradicating lice, mites and ticks from both humans and animals, as well as eliminating fleas from animals. Furthermore, when applied directly to the skin for use as an insect repellant, virtually 100% of all mosquito types tested were effectively repelled from the skin surfaces on which the compositions of the present invention were applied.

In Table II, one preferred formulation of the present invention for an insecticide employable on plants, trees, crops, etc. is provided. As shown therein, these formulations comprise aqueous solutions of Triethanolamine Lauryl Sulfate and Cocoamphocarboxyglycinate.

TABLE II

Insecticide Composition for Plants, Crops, Trees, etc.

| Ingredient | Quantity (% by Vol.) |
|---|---|
| Triethanolamine Lauryl Sulfate | 0.3–0.6 |
| Cocoamphocarboxyglycinate | 0.1–0.2 |
| Water | Balance |

Cocoamphocarboxyglycinate, as employed in the preferred insecticide compositions detailed in Table II, is also known by the CTFA designation of Disodium Cocoampbodiacetate. This compound is an amphoteric organic compound that conforms to the following formula:

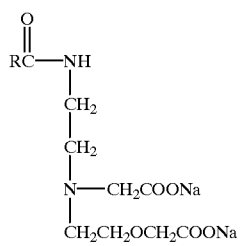

where RCO— represents the fatty acids derived from coconut oil.

By employing the composition defined in Table II, a highly effective insecticide is achieved for application to a wide variety of plants, trees, crops, etc. Preferably, this composition is applied as a spray. As detailed in the following examples, this composition has been found to be particularly effective in killing a wide variety of insects in the *phylum Arthropoda*, particularly stink bugs, caterpillars, most ants, most flies, including fruit flies and white flies, aphids, mealy bugs, and the like.

If desired, the insecticide composition detailed in Table II can be prepared as a concentrate incorporating the desired relative quantities of Triethanolamine Lauryl Sulfate and Cocoamphocarboxylglycinate. The concentrate can be maintained in this form for extended time periods and diluted with the appropriate amount of water when desired for use. In this way, storage of the insecticide composition is attained in a more convenient manner, due to the substantially reduced quantity needed for storage in the undiluted form.

In most application situations, the insecticides of Table II are used as a spray in a single application, preferably under dry conditions. All of the foliage of the plant, crop, tree, etc. is sprayed with the insecticide in order to kill the unwanted insects. Any resistant insects can be safely eliminated in a second application which is made between about 30 minutes and 24 hours after the first application. By employing this procedure, safe and trouble-free eradication of unwanted insects is obtained.

In Table III, a further alternate insecticide composition is provided which has been found to be highly effective for use on plants, crops, trees, and the like.

TABLE III

Insecticide Composition for Plants, Crops, Trees

| Ingredient | % by Vol. |
|---|---|
| Compound as defined by Formula I | 0.05–0.7 |
| Triethanolamine Dodecylbenzenesulfonate | 0.05–0.4 |
| Ammonium Hydroxide | 0–0.02 |
| Sodium Lauryl Sulfate | 0–0.03 |
| Laureth -4 | 0–0.02 |
| Water | Balance |

As detailed in Table III, the principal ingredients of this insecticide composition comprise triethanolamine dodecylbenzenesulfonate and an ethanolamine formative defined by Formula I. Preferably, the ethanolamine formative of Formula I comprises one or more selected from the group consisting of monoethanolamine, diethanolamine, coconut diethanolamide and coconut polyethanolamide. In addition to these principal ingredients, the additional additives detailed in TABLE III can be employed, if desired.

It has been found that this insecticide composition is preferably prepared by mixing the ethanolamine formative of Formula I with the triethanolamine dodecylbenzenesulfonate and the laureth –4, if employed, into water and heating the composition to 50° C. After heating to this temperature, the aqueous solution is allowed to cool. Once the aqueous solution has reached room temperature, the ammonium hydroxide and sodium lauryl sulfate, if employed, are added to the composition.

If desired, the insecticide composition may be prepared as a concentrate and stored for future use. In this way, whenever application is needed, the concentrated composition is diluted with water prior to application to the desired plants, crops, trees, etc.

In this regard, it has been found that the concentrated solutions of the insecticide composition of TABLE III preferably are formulated to be diluted at the rate of about 1 part of insecticide concentrate for every 200 parts of water. In this way, the desired dilution of the concentrated insecticide composition is realized and safe, non-hazardous application of the composition to the desired plants, crops, trees, etc. is attained, while still realizing the desired elimination and/or control of the unwanted insects.

BEST MODE FOR CARRYING OUT THE INVENTION

In order to demonstrate the unique capabilities of the present invention and prove the efficacy of the insecticide and insect repellents detailed herein, the following examples are provided. In addition to providing the requisite support for the present invention, these examples are intended as a teaching of the best mode for carrying out the present invention. However, these examples are intended as representative samples of the overall compositions of this invention and are not intended to limit, in any manner, the breadth or scope of the present invention.

In Tables IV, V, and VI, numerous examples are provided detailing alternate compositions for the insecticide and insect repellant compositions of the present invention for application to humans and animals. Each of the compositions detailed in Tables IV, V, and VI were separately prepared and independently tested to show the efficacy of each composition. In addition, numerous other tests were conducted with varying compositions, with the examples provided being representative samples of the testing program which was conducted.

TABLE IV

| INGREDIENT | EXAMPLES (% BY VOL.) | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Monoethanolamine | | | | | | 20 | 25 | 10 | 35 | 50 | | | | | |
| Diethanolamine | 20 | 25 | 10 | 35 | 50 | | | | | | | | | | |
| Triethanolamine | | | | | | | | | | | 20 | 25 | 10 | 35 | 50 |
| Water | 80 | 75 | 90 | 65 | 50 | 80 | 75 | 90 | 65 | 50 | 80 | 75 | 90 | 65 | 50 |

TABLE V

| INGREDIENT | EXAMPLES (% BY VOL.) | | | | | | | | | |
|---|---|---|---|---|---|---|---|---|---|---|
| | 16 | 17 | 18 | 19 | 20 | 21 | 22 | 23 | 24 | 25 |
| Coconut Diethanolamide | 20 | 25 | 10 | 35 | 50 | | | | | |
| Coconut Polydiethanolamide | | | | | | 20 | 25 | 10 | 35 | 50 |
| Water | 80 | 75 | 90 | 65 | 50 | 80 | 75 | 90 | 65 | 50 |

TABLE VI

| INGREDIENT | EXAMPLES (% BY VOL.) | | | | | | | | | | |
|---|---|---|---|---|---|---|---|---|---|---|---|
| | 26 | 27 | 28 | 29 | 30 | 31 | 32 | 33 | 34 | 35 | 36 |
| Monoethanolamine | | | | | | | | | | | |
| Diethanolamine | 33.3 | 20 | 25 | 10 | 5 | | | | | | |
| Triethanolamine | 33.5 | 20 | 25 | 10 | 5 | 33.3 | 20 | 25 | 10 | 5 | 33.3 |
| Coconut Diethanolamide | | | | | | 33.3 | 20 | 25 | 10 | 5 | |
| Coconut Polydiethanolamide | | | | | | | | | | | 33.3 |
| Water | 33.4 | 60 | 50 | 80 | 90 | 33.4 | 60 | 50 | 80 | 90 | 33.4 |

TABLE VI-continued

| INGREDIENT | 37 | 38 | 39 | 40 | 41 | 42 | 43 | 44 | 45 | 46 |
|---|---|---|---|---|---|---|---|---|---|---|
| Monoethanolamine |  |  |  |  | 5 | 33.3 | 5 | 33.3 | 5 | 15 |
| Diethanolamine |  |  |  |  |  |  |  |  |  |  |
| Triethanolamine | 20 | 25 | 10 | 5 |  |  | 5 | 33.3 |  |  |
| Coconut Diethanolamide |  |  |  |  | 5 | 33.3 |  |  | 5 | 30 |
| Coconut Polydiethanolamide | 20 | 25 | 10 | 5 |  |  |  |  | 5 | 15 |
| Water | 60 | 50 | 80 | 90 | 90 | 33.4 | 90 | 33.4 | 85 | 40 |

Each of the formulation examples detailed in Tables IV, V, and VI were separately prepared and tested in order to evaluate the capabilities of each composition as an insecticide, as well as an insect repellant. In most instances, where possible, each formulation was prepared and tested as a spray, shampoo and lotion. In addition, each of these compositions was specifically tested and evaluated against insects such as mosquitoes, ticks, fleas, mites, and lice.

In conducting one group of tests, heavily flea-infested dogs were treated with each of the formulation examples detailed in Tables IV, V, and VI (except for Examples 6–10) to determine the ability of each composition to eradicate the fleas. Each of the compositions were applied as a shampoo and a spray which was thoroughly worked into the fur of the dog and then rinsed out. Observations revealed that the fleas died virtually immediately on contact with the composition being employed, with no remaining flea infestation being observed. Although all of the formulations tested worked successfully, the best results were obtained from the formulations of Examples 1–5 and 11–20.

Each of the compositions also successfully eliminated mange mites, with the mites being eradicated after completion of the shampoo/spray application and washing thereof. Observations revealed that the mange was cleared of all mites, with new hair growth occurring at less than two weeks.

In order to evaluate the ability of the formulations defined in Tables IV, V, and VI to eradicate and control lice, each of the formulations, except for Examples 6–10, were separately applied to different individuals, all of whom were members of three different families. The ages of these individuals ranged from four years to fifty-five years, with each individual being severely infested with hair lice. Each formulation was administered as a shampoo, which was thoroughly worked into the hair and then rinsed out.

After the application of each formulation, the hair fibers of each of the individuals were carefully observed. In each instance, infestation of the lice appeared to have been eliminated with a single shampoo application. In addition, many of the eggs attached to the hair shafts were loosened but, in many instances, remained attached to the hair fibers.

A follow-up shampoo was performed on each individual between about three and seven days after the initial shampoo application. Observations after the second shampoo application revealed, in each instance, virtual complete removal of all remaining eggs from the hair fibers. Although each of the formulations were successful, the best results were obtained from formulation Examples 1–5 and 16–20.

Six individuals were instructed to continue to use the shampoo on a continuing basis, while the remaining individuals were not so instructed. The six individuals who continued to use the shampoo of the present invention had no re-infestation occur during the testing time period. However, the individuals who did not continue to use the shampoo product of the present invention experienced lice re-infestation within two to four weeks.

It is important to note that the individuals selected for this test typically experience lice infestation due to the close quarters and poor living conditions of these individuals. Consequently, re-infestation would normally occur and would be expected, while remaining fee from infestation is unexpected and further proved the efficacy of the formulations of the present invention.

In order to evaluate the ability of the formulations of the present invention to effectively repel mosquitoes, formulation Examples 1–3, 6–13, 16–18, 21–23, 29, 30, 34, 35, 39 and 40 detailed in Tables IV, V, and VI were applied, as a lotion, to a group of construction workers, on a daily basis for ten days. Each of the treated individuals worked in a mosquito infested area.

Each individual, regardless of the composition employed, experienced only an occasional mosquito bite, while employing the formulations of this invention. Prior to using the formulations of the present invention, the individuals experienced continuous mosquito bites to the extent that their ability to work was being hampered.

Throughout the test period, each individual wore only shorts without any shirts or socks. In addition, each of the compositions was found to effectively repel the mosquitoes for between about four and eight hours, depending upon the humidity level and the perspiration level of the individual.

Similar experiments were also conducted with other individuals over time periods ranging from three days to three months in order to evaluate both the efficacy and the long-term effect of the compositions. In each instance, virtually complete mosquito repellency was realized without any adverse or unwanted side effects ever occurring.

In order to determine the capability of the formulas detailed in Tables IV, V, and VI to effectively control ticks, each of the compositions, except for Examples 6–15, were separately tested on both calves and female adult Holstein cows. This particular breed was selected since they appear to be most susceptible to ticks.

Prior to applying the compositions, the animals were evaluated with the calves having twenty-five ticks per calf, while the adult cows had about fifteen hundred ticks per animals. Each of the compositions were applied to these animals as a spray, followed by visual observation.

After the first application, numerous ticks remained on all of the treated animals. The spray was then reapplied on the second day, and again on the third day. After the third application, the calves were about 90% free of ticks, while the adult cows were roughly 70% clean. Although many of the ticks on the adult cows were dead, some ticks did remain clinging to the animal.

No further application of the compositions were made to the cows, but daily observations were conducted. Within one week after the initial spray application, both the adult cows and calves were 90 to 95% free of all ticks. This was achieved with no further application beyond the three consecutive sprays. Although all of the compositions tested were effective in eradicating ticks, formulation Examples 1 and 3 were the most effective.

The tests conducted revealed that the compositions defined by Examples 4, 5, 15, and 26–28 did work substantially faster in killing the ticks when compared to the other spray formulations. However, after a second application of these compositions, irritated areas around the cows neck and head were observed. As a result, the formulations were washed off.

Further observations of the test animals revealed that both the adults and the calves remained free of ticks for several weeks after the application of the compositions shown in Tables IV, V, and VI. During the testing time period, rainy days occurred in regular intervals of about three to five days. The day-time temperature ranged between about 80° and 85° F. with the nighttime temperature between about 65° and 70° F.

In Tables VII and VIII, additional examples of alternate compositions constructed in accordance with the present invention are detailed. These alternate compositions define insecticides formulated for application to plants, trees, crops, etc.

TABLE VII

| INGRE-DIENT | Example | | | | |
|---|---|---|---|---|---|
| | 47 | 48 | 49 | 50 | 51 |
| Triethanolamine Lauryl Sulfate | 300 ml. | 400 ml. | 500 ml. | 600 ml. | 200 ml. |
| Cocoamphocarboxyglycinate | 100 ml. | 150 ml. | 200 ml. | 240 ml. | 100 ml. |
| Water | 100 L. | 100 L. | 100 L. | 100 L. | 100 L. |

TABLE VIII

| INGREDIENT | Example | |
|---|---|---|
| | 52 | 53 |
| Monoethanolamine | 100 cm.$^3$ | 100 cm.$^3$ |
| Coconut Diethanolamide | 200 ml. | |
| Coconut Polyethanolamide | 300 ml. | |
| Triethanolamine Dodecylbezenesulfonate | 100 ml. | 150 ml. |
| Lauryl Alcohol | 12 ml. | 1 ml. |
| Ammonium Hydroxide | | 12 ml. |
| Sodium Lauryl Sulfate | | 40 ml. |
| Water | 100 L. | 200 L. |

In order to determine the efficacy of each of the compositions detailed in Tables VII and VIII, each composition was separately prepared and independently tested using numerous different types of plants. In conducting these tests, each of the formulations detailed in TABLES VII and VIII, were separately prepared and tested on over sixty different types of ornamental plants. In general, the formulations detailed in Examples 47, 48, 49 and 50 were the most effective in eliminating all undesirable insects, while causing absolutely no harm to any plant.

In these tests, it was found that formulations of Example 48 is preferred. In evaluating the tests conducted, it was found that the formulation of Example 48 provided an overall greater improvement than the formulation of Example 47, while the formulations of Examples 49 and 50 were substantially similar in efficacy to Example 48. However, in view of finding no increased benefit in using the high concentrations of Examples 49 and 50, the formulation of Example 48 is preferred.

In addition, in conducting these tests, it was discovered that the formulation of Example 51 was substantially less effective than the other formulations detailed in TABLE VII. Consequently, the formulation of Example 51 is not recommended and the formulations of Examples 47–50 are preferred.

In conducting these tests, the formulations were evaluated both during the hottest months of a typical tropical summer, as well as during the cooler months which are more typical of summers in the northern tier states of the United States. During the tests conducted in the cooler months, it was found that the formulation of Examples 49 and 50 worked with equal efficacy to the formulation of Example 48.

In addition, it was also discovered that the formulation of Example 50 proved particularly effective as an all-purpose household insecticide, with particular efficacy in destroying cockroaches. Although this formulation is the strongest of the formulations of TABLE VII, it is believed that the limited use of this formulation, when employed as a household insecticide, enables this composition to work particularly effectively and, as a result, is preferred for this purpose.

In general, the overall results achieved during the tropical summer months resulted in some limited adverse reactions to the formulations of Examples 49 and 50, while no adverse reactions were found with the formulation of Examples 47, 48, and 51. However, when the same tests were conducted during the cooler months, formulations of Examples 47, 48, 49, and 51 cause no adverse reactions to any of the plants, while the formulations of Example 50 caused some slight adverse effects to certain plants.

It is important to note that the formulations of the present invention, as detailed in TABLE VII can be employed on virtually any blooming plant with virtually no harm resulting to the foliage. Furthermore, these formulations can be employed on crops or fruit trees up to harvest time, without adversely affecting the crop or fruit being produced. No such prior art composition is capable of being used in this way, to this extent.

In addition to the tests detailed above in reference to formulations of TABLE VII, similar tests were also conducted on the formulations detailed in TABLE VIII. In general, these tests show that the formulations of TABLE VIII were toxic, to varying degrees, on most soft leaf plants. However, plants with a waxy cuticle, such as coffee, citrus, crotin, etc., showed no adverse reactions. In conducting these tests, it was found that up to seven days were required for the adverse side effects on the leaf of the plant became apparent. Typically these side effects range from dark speckling of the leaf to actual burning of the leaves.

In order to further demonstrate the efficacy of the compositions of this invention, additional tests were conducted on a group of plants and trees which represent the most sensitive varieties of plants and trees. In this way, any possible adverse effects that may be caused by the formulations detailed in TABLE VII would become immediately apparent when applied to these sensitive plants.

In conducting these tests, each composition defined in TABLE VII was prepared and tested on tea roses—foliage, flowers, and green fruit; impatiens—foliage and flowers; anthurium—foliage and flowers; tomato—foliage; geranium—foliage; lime tree—foliage and flowers; lemon trees—foliage; cabbages—foliage; strawberries—foliage; and poinsettias—foliage and flowers. Of the plants and trees, the most sensitive of all is the poinsettia.

Presently, greenhouses are forced to discard bug-infested poinsettias, as well as similar delicate plants, since no prior art compound can be effectively employed to eliminate the insects, without destroying this sensitive plant. However, as detailed herein, the formulations of the present invention can be effectively employed on poinsettias, as well as on most other plants to effectively eradicate the insects, without causing harm to the foliage of the plants.

These tests were conducted to evaluate the effect on these sensitive plants of repeated heavy applications of each of the formulas on a daily basis. Observations of both the plant foliage and the flowers were made on a daily basis. All of the tests were performed outdoors and all plants were thoroughly soaked with the formula.

All plants were in their natural conditions and were not given any special attention. The soil condition in which the plants and crops grew comprised a sandy-loam composition. During the tropical summertime tests, daytime temperatures averaged between about 85° and 92° F., with the average nighttime temperature ranging between about 75° and 80° F. The average temperature at the time of application of each of the compositions was 85° F.

As is evident from the conditions and plants detailed above, the compositions of the present invention were tested under abnormally difficult conditions and on the most sensitive plants. In this regard, temperatures were at their highest and water tables at their lowest. Furthermore, as is known in the industry, no known compound can be employed effectively on plants in bloom without causing harm to the foliage.

In testing each composition, the plants were sprayed over a five-day time period, with the plants being visually evaluated each day. In each of the experiments, the composition was applied on each day of the five days, except for day 4. Furthermore, each of the days during the five-day experiment were sunny, with light showers occurring at night on day 2. After the five-day application process detailed above, the plants were constantly monitored for one month to observe the resulting effects.

During the five-day application process, no visible foliage damage was observed on any of the plants for any of the compositions detailed in Table VII, except for Example 49, when applied to tomatoes. In this instance, some visible foliage damage was observed, as detailed below.

The impatiens flowers showed no reaction after the first application of the composition of Example 47. However, after the second application of the composition of Example 47, the flowers showed a whitening on their edges. After the further application of the composition of Example 47, the flowers were ruined.

A similar result was observed with the composition of Example 48, after a single application, while the composition of Example 49 produced a slightly more pronounced whitening of the flowers than was observed with Example 48, after the first application. After the second application of both the compositions of Example 48 and Example 49, the flowers were ruined.

The rose flowers showed no reaction to the compositions of Examples 47 and 48 until the third day, at which time, a loss of color at the petal edges was observed. By employing the composition of example 49, the same color loss was observed on day 2.

The tomato flowers showed no adverse reaction to the composition of Examples 47 and 48, while showing sporadic effects from the composition of Example 49. However, the tomato foliage reacted to the application of the composition of Example 49, after the second day, by dark spotting on some leaves.

Finally, the composition of Example 48 produced a minor reaction on the poinsettia flowers after the second day. However, no further damage was observed and the plant continued to appear healthy.

During the one-month monitoring of all of the treated plants, no further foliage or flower changes were observed, and normal growth continued. Furthermore, these observations revealed that each of the compositions defined in Table VII, except for Example 51, successfully killed all flies, aphids, fruit flies, white flies, mealy bugs, mosquitoes, spiders, ants, stink bugs, various caterpillars, squash bugs, and the like, attacking the treated plant during the application time period, while also retaining an insect repellant effect keeping the insects away from the plant for the thirty days after insecticide application.

The identical process detailed above was repeated two weeks after the completion of the first test program. The identical procedures detailed above were followed, and the observations were virtually identical to the observations detailed above.

During the cooler months, which are more typical to the summer months of the northern tier states of the United States, a test program similar to the test program detailed above was conducted. In the test program, the same plants were sprayed over an seven-day time period, with the plants being visually evaluated each day. In each of the experiments, the compositions were separately applied on each day of the seven days, except for day numbers 4 and 5. In addition, days 1, 2, and 3 were sunny, day 4 had thunderstorms with light rain at night, day 5 was cloudy with light rain at night, and days 6 and 7 were cloudy. Throughout the seven days, daytime highs ranged between about 65° F. and 80° F. with an average temperature of 72° F. Nighttime temperatures ranged between about 55° F. and 65° F. After the seven-day application process detailed above, the plants were monitored for one month to observe the resulting effects.

During the seven-day application process, no visible damage was observed on either the foliage or the flowers of any of the plants for any of the compositions detailed in TABLE VII, except for Example 50. With this one composition, some visible damage was observed as detailed below.

On day 2, slight discolored edges of tea rose flowers were observed, while pronounced discoloring was found on day 3. On day 4, the tea rose flowers were ruined. In addition, the impatiens flower showed discolored edges on the second day and were ruined on the third day. The tomato foliage showed slight speckling on the underside of the leaves on the third day, with no further change being observed until the seventh day when more pronounced spotting was noted. Finally, the geranium foliage showed slight speckling on the underside of the leaf on the sixth day with no further damage occurring.

During the one-month monitoring of all of the treated plants, no further foliage or flower changes were observed and normal growth continued. Furthermore, these observations revealed that each of the compositions defined in Table VII, except for Example 51, successfully killed all flies, aphids, fruit flies, white flies, mealy bugs, mosquitoes, spiders, ants, stink bugs, caterpillars, squash bugs, and the like attacking the treated plant during the application time period, while also retaining an insect repellant effect keeping the insects away from the plant for the thirty days after the insecticide application.

This identical process was also repeated two weeks after completion of the previous test program. The identical procedures detailed above were followed, and the results obtained were virtually identical to the initial results detailed above.

Based upon the foregoing test procedures of the composition defined in TABLE VII, it is apparent that each of the compositions defined in Table VII comprises a highly effective insecticide which provides safe, trouble-free application to the plants and crops with only minor damage being observed in some instances. The overall results showed that the composition defined in Example 48 was preferred for the best all-round performance, since it possessed the optimum combination of insect killing capabilities, while being the most non-injurious to the plants.

Although the composition of Example 48 is preferred, the remaining compositions in TABLE VII, except for Example 51, are believed to be substantially equally effective in providing the desired insecticide effects in a substantially safe and trouble-free manner. Furthermore, each of the compositions defined in TABLE VII, are believed to comprise excellent products for both commercial and household use, since each composition is easy to handle and apply, while having no noticeable, unpleasant odor.

As previously discussed, the compositions detailed in TABLE VIII were effective in controlling insects, but were slightly phytotoxic to soft leafed plants. However, even though the compositions of TABLE VIII proved to have more adverse reactions with plants than the compositions of TABLE VII, the compositions defined in TABLE VIII are also believed to comprise highly effective insecticides which can be employed in a safe and trouble-free manner. Furthermore, the compositions of TABLE VIII comprise excellent products for both commercial and household use since these compositions are easy to handle and apply, having no noticeable unpleasant odor, and provide results which are substantially superior to prior art insecticides.

It is believed that the compositions detailed in TABLES VII and VIII comprise the safest insecticide contact sprays that have been developed which is non-injurious to man, animal, or the environment, as well as to the plants upon which the compositions are employed. Clearly, the prior art drawbacks and difficulties that are presently found in toxic, harmful, compositions has been completely eliminated, and a safe-trouble free insecticide composition is realized.

It will thus be seen that the objects set forth above, among those made apparent from the preceding description, are efficiently attained and, since certain changes may be made in the composition detailed herein, as well as in carrying out the process described above, without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

Having described our invention what we claim as new and desire to secure by Letters Patent is:

1. A method for repelling mosquitos comprising the steps of:

A. forming a mosquito repellant which is non-toxic, environmentally safe, and specifically formulated for application to the skin surface of humans, said repellant comprising:
      a. between about 10% and 50% by volume of the total composition of one or more compounds selected from the group consisting of coconut diethanolamide, and coconut polydiethanolamide, and
      b. water forming the balance;
   B. rubbing the mosquito repellant on the skin surface of an individual substantially covering the skin surface to be exposed to mosquitos, and
   C. repeating step B on a daily basis whenever exposure to mosquitos is likely.

2. The method defined in claim 1, wherein said mosquito repellant is further defined as consisting essentially of between about 10% and 25% by volume of the total composition of triethanolamine and coconut diethanolamide, with water forming the balance.

3. The method defined in claim 1, wherein said mosquito repellant is further defined as consisting essentially of
   a. between about 5% and 10% by volume of the total composition of triethanolamine;
   b. between about 5% and 10% by volume of the total composition of one selected from the group consisting of coconut diethanolamide, and coconut polydiethanolamide, and
   c. water forming the balance.

4. The method defined in claim 1, wherein said repellant is further defined as consisting essentially of:
   a. between about 5% and 25% by volume of the total composition of one or more compounds selected from the group consisting of coconut diethanolamide, and coconut polydiethanolamide,
   b. between about 5% and 25% by volume of the total composition of one or more compounds selected from the group consisting of monoethanolamine, and triethanolamine; and
   c. water forming the balance.

5. A method for repelling mosquitos comprising the steps of:

A. forming a mosquito repellant which is non-toxic, environmentally safe, and specifically formulated for application to the skin surface of humans, said repellant consisting essentially of
      a. between about 5% and 10% by volume of the total composition of triethanolamine;
      b. between about 5% and 10% by volume of the total composition of coconut diethanolamide, and
      c. water forming the balanace;
   B. rubbing the mosquito repellant on the skin surface of an individual substantially covering the skin surface to be exposed to mosquitos, and
   C. repeating step B on a daily basis whenever exposure to mosquitos is likely.

* * * * *